United States Patent [19]

Schaller et al.

[11] Patent Number: 4,605,512

[45] Date of Patent: Aug. 12, 1986

[54] SMALL PEPTIDES WITH THE SPECIFICITY OF FOOT AND MOUTH DISEASE VIRAL ANTIGENS

[75] Inventors: Heinz E. Schaller, Heidelberg; Eberhard P. Pfaff, Schwaigern-II, both of Fed. Rep. of Germany

[73] Assignee: Biogen N.V., Curacao, Netherlands

[21] Appl. No.: 478,901

[22] Filed: Mar. 25, 1983

[30] Foreign Application Priority Data

Mar. 26, 1982 [GB] United Kingdom ............... 8209041

[51] Int. Cl.[4] ............................................. C07C 103/52
[52] U.S. Cl. ............................ 260/112.005; 530/326; 530/806; 424/89
[58] Field of Search .............................. 260/112.5 R

[56] References Cited

FOREIGN PATENT DOCUMENTS 0040922 12/1981 European Pat. Off. .
0044710 1/1982 European Pat. Off. .
0063953 11/1982 European Pat. Off. .

OTHER PUBLICATIONS

Virology 52, 520–528 (1973).
FEBS Letter 157, (1983) 261–264.
Nature 298, (1982) 30–33.
J. Gen. Virol. (1977) 34, 397–400.
Chem. Abstr. vol. 98, 1983, 84264y.
Chem. Abstr. vol. 84, 1976, 175491x.
Chem. Abstr. vol. 77, 1972, 123642h.
Chem. Abstr. vol. 98, (1983), 157543a.
Chem. Abstr. vol. 77, (1972), 31312x.
Chem. Abstr. vol. 99, (1983), 136708p.

*Primary Examiner*—Delbert K. Phillips
*Attorney, Agent, or Firm*—James F. Haley, Jr.

[57] ABSTRACT

Small peptides that display the specificity of FMD viral antigens. The peptides are useful in compositions and methods for the protection of animals for at least some time from FMD viral infections. The peptides of this invention may be prepared by conventional synthetic methods, recombinant DNA technology or a combination of the two. They may also be modified in composition and conformation to improve further their specific antigenic properties.

1 Claim, 2 Drawing Figures

|       | 1                                         10                    20                    30                    40 |
|-------|------------------------------------------------------------------------------------------------------------------|
| FMDV C₁   | T T T T T E S A D P V T T T T V E N Y G G E T Q V Q R R H H T D V A F V L D R F V - - * |
| FMDV O₁K  | T T S A G E S A D P V T T T V E N Y G G E T Q I Q R R Q H T D V S , F I M D R F V - - * |
| FMDV A₁₂  | T T A T G E S A D P V T T T T V E N Y G G E T Q V Q R R H H T D V S F I M D R F V - - * |
| FMDV A₁₀  | T T T T G E S A D P V T T T T V E N Y G O D T Q V Q R R H H T D V G F I M D R F V - - * |
| FMDV A₅   | - - - - - - - - - - - - - - - - - - - - - - - - - - - - - - - - - - - - - - - - - - * |
| FMDV A₂S  | T T A S G E S A D P V T T T T V E N Y G G E T - - - - - - - - - - - - - - - - - - - - * |

|       | 41                                        50                    60                    70                    80 |
|-------|------------------------------------------------------------------------------------------------------------------|
| FMDV C₁   | K V T V S G N Q H T L D V M Q A H K D N I V G A L L R A A T Y Y F S D L E I A V - - * |
| FMDV O₁K  | K V T P Q N Q I N I L D L M Q I P S H T L V G A L L R A S T Y Y F S D L E I A V - - * |
| FMDV A₁₂  | K I K S L N P T H V I D L M Q T H Q H G L V G A L L R A A T Y Y F S D L E I V V - - * |
| FMDV A₁₀  | K I N S L S P T H V I D L M Q T H K H G I V G A L L R A A T Y Y F S D L E I V V - - * |
| FMDV A₅   | - - - - - - - - - - - - - - - - - - - - - - - - - - - - - - - - - - - - - - - - - - * |
| FMDV A₂S  | - - - - - - - - - - - - - - - - - - - - - - - - - - - - - - - - - - - - - - - - - - * |

|       | 81                                        90                   100                   110                  120 |
|-------|------------------------------------------------------------------------------------------------------------------|
| FMDV C₁   | T H T G K L T W V P N G A P V S A L D N T T N P T A Y H K G P L T R L A L P Y T - - * |
| FMDV O₁K  | K H E G D L T W V P N G A P E K A L D N T T N P T A Y H K A P L T R L A L P Y T - - * |
| FMDV A₁₂  | R H D G N L T W V P N G A P E A A L S N T G N P T A Y N K A P F T R L A L P Y T - - * |
| FMDV A₁₀  | R H D G N L T W V P N G A P E A A L S N T S N P T A Y N K A P F T R L A L P Y T - - * |
| FMDV A₅   | - - - - - - - - - - - - - - - - - - - - - - - - - - - - - - - - - - - - - - - - - - * |
| FMDV A₂S  | - - - - - - - - - - - - - - - - - - - - - - - - - - - - - - - - - - - - - - - - - - * |

FIG. 1

```
        121                  130                140                    150                160
FMDV C1   A P H R V L A T G Y T G T T T Y - - T A - - S T R G D L A H L T A T R A G H L P
FMDV O1K  A P H R V L A T V Y N G E C R Y N R N A V P N L R G D L Q V L A Q K V A R T L P
FMDV A12  A P H R V L A T V Y N G T N K Y S A S G S - G V R G D F G S L A P R V A R Q L P
FMDV A10  A P H R V L A T V Y D G T N K Y - - S A S D S R S G D L G S I A A R V A T Q L P
FMDV A5   A P H R V L A T V Y N G T N K Y S - T G G P - R R R G D M G S A A A R A A K Q L P
FMDV A2S  * * * * * * * * * * * * * * * * * * * * * * * * * * * * * * * V A T Q L P 161                  170                180                    190                200
FMDV C1   T S F N F G A V K A E T I T E L L V R M K R A E L Y C P R P I L P I Q - P T G D
FMDV O1K  T S F N Y G A I K A T R V T E L L Y R M K R A E T Y C P R P L L A I H - P T E A
FMDV A12  A S F N Y G A I K A E T I H E L L V R M K R A E L Y C P R P L L A I E V S S Q D
FMDV A10  A S F N Y G A I Q A Q A I H E L L V R M K R A E L Y C P R P L L A I K V T S Q D
FMDV A5   A S F N Y G I I R A - T I L E L L V R L K R A E L Y C P R P L L A I D V S S Q D
FMDV A2S  A S F N Y G A I R A Q T I H E L L V R M * * A E L Y C P R P L L A I - - - - -

201                  210
FMDV C1   R H K Q P L V A P A K Q L L
FMDV O1K  R H K Q K I V A P V K Q T L
FMDV A12  R H K Q K I I A P G K Q - L
FMDV A10  R Y K Q K I I A P A K Q L L
FMDV A5   R H K Q K I I A P A R Q L I
FMDV A2S  - - - - - - - - - - - - - -
```

FIG. 2

SMALL PEPTIDES WITH THE SPECIFICITY OF FOOT AND MOUTH DISEASE VIRAL ANTIGENS

TECHNICAL FIELD OF INVENTION

This invention relates to small peptides with the specificity of foot and mouth disease ("FMD") viral antigens. More particularly, the invention relates to small peptides which comprise the antigenic determinants of one or more serotypes of foot and mouth disease virus ("FMDV") and the use of these peptides in compositions and methods for rendering animals resistant to FMDV for at least some period of time.

BACKGROUND ART

FMD virus is a picornavirus which affects cloven-footed animals. It is one of the most infectious and easily transmitted diseases of livestock. The disease is generally characterized by vesicular lesions on the feet and mouth of the infected animal. Deterioration in body condition generally lowers production of animal products by 25%. Epizootics of FMDV cause major economic losses in the production and marketing of meat, dairy products, wool, hides and other commodities. For example, during an epizootic in Great Britain in 1967–68 nearly 500,000 infected or exposed cattle, swine, sheep and goats were destroyed in the process of eradicating the disease.

There are seven distinct serotypes of FMD virus. These are the European or classical types O, A and C, the Southern African Territories types SAT1, SAT2 and SAT3 and the Asian type I. E.g., K. J. H. Robson et al., "An Assessment By Competition Hybridization Of The Sequence Homology Between The RNAs Of The Seven Serotypes Of FMDV", 37 *J. Gen. Virol.* 271–76 (1977). Types O, A and C have been found in Europe, South America, Asia and the northern part of Africa, although the range is extending. The three Southern African Territories types were first detected in Southern Africa, but again the disease type is spreading in geographic location. The Asian type occurs in Asian countries from the Eastern Mediterranean to the Far East. Each of these serotypes is also comprised of several serological subtypes.

Vaccines to protect animals from FMDV are available. Most commonly these vaccines comprise inactivated or attenuated whole virus. They are administered under known schedules and regimes on an annual or quarter-annual basis. Because the seven virus types display a lack of cross-immunity (Robson et al., supra) and different areas of the world have a different spectrum of virus types, vaccination is sometimes carried out with a bivalent or trivalent material. However, this is not always necessary or advisable.

Production of FMD whole virus vaccines is beset by several major difficulties. First, because of the infectious character of the virus, laboratory growth of virus for vaccines must be done in isolated facilities under high containment. Second, the virus-based vaccines often display an unacceptable variation in potency after production and inactivation. Third, the vaccines must be tested under very controlled conditions to insure proper efficiency of attenuation or inactivation. Otherwise, the vaccine may cause accidental active infection or subacute progressive disease in the treated animals. All of these production problems result in higher costs for the ultimate vaccine. In addition to the above-described production problems, the use of whole-virus vaccines results in a small, but a significant, number of allergic side reactions in the treated animals. These undesirable side effects are probably caused by the many irrelevant antigenic determinants of the viral and non-viral proteins that usually contaminate viral vaccines.

One approach to avoid some of the problems inherent in the production and use of whole virus vaccines is to employ viral subunit vaccines comprising the capsid proteins of FMD virus. E.g., U.S. Pat. No. 4,140,763; H. L. Bachrach et al., "An Experimental Protein Vaccine For Foot-And-Mouth Disease", in 10 *Perspectives in Virology* 147–59 (M. Pollard ed. 1978).

FMD virus is characterized by four capsid proteins, identified as VP1, VP2, VP3 and VP4. The capsid proteins of FMD virus collectively protect the viral ribonucleic acid ("RNA") core of the virus against various inactivating agents. The neutralizing antigen of FMDV seems to be embodied in the VP1 polypeptide (VP3 in United States terminology) (H. L. Bachrach et al., "An Experimental Subunit Vaccine For Foot-And-Mouth Disease", *International Symposium On Foot-And-Mouth Disease*, Lyon 1976, 35 *Develop. Biol. Standard* 155–60 (1977)). Moreover, it has been reported that the antigenic portion of VP1 appears to reside in the last ⅓ of the protein, i.e., nearest its COOH terminus (R. Franz et al., "Localization And Characterization Of Two Immunogenic Regions On The Coat Protein VP$_{Thr}$ Of Foot-And-Mouth Disease Virus (FMDV) Subtype O$_1$K Inducing Neutralizing Antibodies", Münich (December 1980)). It has also been reported that two enzyme-sensitive areas of VP1 appear to exist—between sequence positions 138–154 and between positions 200–213 [K. Strohmaier et al., "Localization And Characterization Of The Antigenic Portion Of The FMDV Immunizing Protein", presented at the "Positive Strand Virus" session at the meeting of the Society for General Microbiology, Cambridge (April 1981)]. VP1 has been purified and employed to vaccinate swine against challenges by virus (H. L. Bachrach et al., supra). However, at least 10 times more protein than virus-based vaccines were required to effect immunization. Therefore, two or more vaccinations with the VP1 protein-based subunit virus are usually required to protect an animal from FMD virus.

The use of subunit vaccines eliminates to some extent antibody formation against the many irrelevant antigenic determinants of the viral and non-viral proteins that often contaminate viral vaccines. Their use may therefore lessen the possible side effects of viral vaccines. Further, the subunit vaccines are devoid of viral nucleic acid and therefore presumably without risk of causing active infection or subacute progressive disease in the treated herds. However, while these subunit vaccines avoid some of the problems which characterize whole virus-based vaccines, there are also disadvantages in their use. First, to obtain the capsid protein, virus must be cultured and grown. Therefore, the isolated facilities and high production containment attendant to FMD virus growth are not avoided. Second, the proteins must be separated from the virus and highly purified. This process is both slow and expensive. Moreover, if the proteins are not sufficiently purified, the resultant vaccine may still contain enough virus to cause accidental infection or subacute disease.

To avoid the problems that disadvantage the above-described VP1-based vaccines, recombinant DNA technology has also been employed to produce recombinant DNA molecules characterized by a DNA sequence or fragment thereof coding for a polypeptide displaying FMDV antigenicity. This work, conducted jointly by Biogen N.V. and the Max-Planck-Institute for Biochemistry, is described in European patent application No. 40,922. Using the recombinant DNA molecules described in that application, FMD viral-specific nucleotide sequences and FMDV antigenic polypeptides were produced without the necessity of growing large amounts of virus, purifying proteins from the virus or inactivating or attenuating the virus. The antigenic polypeptides and DNA sequences described in that application are useful in compositions and methods for the treatment of FMD virus infection.

Vaccines against FMDV that are based on bacterially-made VP1, accordingly, are much advantaged over vaccines that are based on live virus or proteins isolated from live virus. However, such bacterially-made VP1-based vaccines may be even further improved by replacing the complete VP1 active component in those vaccines with an active component comprising substantially only the antigenic portion of VP1. Such modification of the vaccine results in several compositional and process advantages. The vaccine will contain only a single, or at most very few, antigenic sites. The substantial absence of non-FMDV specific determinants will further reduce the possibility of allergic side reaction in treated animals. The use of smaller peptides will also permit manufacture of a vaccine that will contain a much higher ratio of active component to weight than the previous whole VP1-based vaccines. And, if the antigenic portion of VP1 is prepared by chemical synthesis, its purification will be easier and the resulting vaccine will be a non-biological product. Finally, the smaller peptides may be more easily modified in composition and conformation than the former polypeptides so as to improve further the activity of those polypeptides and the vaccine based upon them.

The potential of identifying and preparing immunologically-active small peptides has been demonstrated. E.g., F. A. Anderer et al., "Properties Of Different Artificial Antigens Immunologically Related To Tobacco Mosaic Virus", 97 *Biochim. Biophys. Acta* 503-09 (1964); H. Langbeheim et al., "Antiviral Effect On MS-2 Coliphage Obtained With A Synthetic Antigen", 73 *Proc. Natl. Acad. Sci. USA* 4636-40 (1976); F. Audibert et al., "Active Antitoxic Immunization By A Diphtheria Toxin Synthetic Oligopeptide", 289 *Nature* 593-94 (1981); E. H. Beachey et al., "Type-specific Protective Immunity Evoked By Synthetic Peptide Of *Streptococcus pyogenes* M Protein", 292 *Nature* 457-59 (1981); and G. M. Müller et al., "Anti-Influenza Response Achieved By Immunization With A Synthetic Conjugate", 79 *Proc. Natl. Acad. Sci. USA* 569-73 (1982).

In addition, the amino acid sequences of antigenic polypeptides determined using recombinant DNA technology have been employed to predict areas of possible antigenicity. The peptides defined by those areas have then been synthesized and their immunological characteristics analyzed. For example, the amino acid sequence of the surface antigen of hepatitis B virus predicted from the nucleotide sequence of the gene coding for that antigen was analyzed to predict the internal and external residues of the antigen and a series of peptides were prepared based on those predictions. R. A. Lerner et al., "Chemically Synthesized Peptides Predicted From The Nucleotide Sequence Of The Hepatitis B Virus Genome Elicit Antibodies Reactive With The Native Envelope Protein Of Dane Particles", 78 *Proc. Natl. Acad. Sci. USA* 3403-07 (1981); T. P. Hopp, "A Synthetic Peptide With Hepatitis B Surface Antigen Reactivity", 18 *Molec. Immun.* 869-72 (1981); G. R. Dreesman et al., "Antibody To Hepatitis B Surface Antigen After A Single Inoculation Of Uncoupled Synthetic HBsAg Peptides", 295 *Nature* 158-60 (1982); European patent application No. 44,710.

A similar analysis and synthesis has also been described in European patent application No. 44,710 for preparing small peptides as antigens against FMDV subtype $O_1K$. As a result of that analysis, five peptides were reportedly prepared—peptide 1: amino acids 1-18 of VP1; peptide 2: amino acids 9-24; peptide 3: amino acids 17-32; peptide 4: amino acids 25-41; and peptide 5: amino acids 21-41. See, e.g., C. Kurz et al., "Nucleotide Sequence And Corresponding Amino Acid Sequence Of The Gene For The Major Antigen Of Foot And Mouth Disease Virus", 9 *Nucleic Acids Research* 1919-31 (1981). These peptides were stated to carry the specific antigenic determinants of FMDV (European patent application No. 44,710).

In addition, the amino acid sequence of VP1 determined by recombinant DNA technology has been employed with an enzyme cleavage pattern for natural VP1 of FMDV subtype $O_1K$. As a result, a series of VP1-derived fragments were localized along the protein (Strohmaier et al., supra). The reported fragments were stated to comprise the following amino acid sequences of natural VP1 of FMDV subtype $O_1K$: 1-9, 10-36, 1-138, 1-145, 37-54, 55-180, 146-213, 155-200 and 181-213. Only fragments 55-180, 146-213, and 181-213 were said to induce neutralizing antibodies. Accordingly, the sequence positions between 138-154 and between 200-213 were predicted to be the antigenic portions of VP1 of FMDV subtype $O_1K$, because those were the only regions in antibody inducing agents not overlapped by non-inducing areas (Strohmaier et al., supra).

DISCLOSURE OF THE INVENTION

The present invention solves the problems referred to above by providing small peptides with the specificity of FMDV viral antigens. Moreover, those peptides produce antisera which are capable of neutralizing FMDV virus in conventional assays and protecting test animals against viral challenge.

The peptides of this invention comprise only a single, or at most a very few, antigenic sites. The substantial absence of non-FMDV specific determinants in the peptides of this invention reduces the possibility of allergic side reactions of treated animals caused by irrelevant determinants. The peptides of this invention, because of their small size, also permit the preparation of vaccines and the attainment of methods of treatment wherein the ratio of active vaccine component to weight is much higher than in previously-available vaccines and methods. Moreover, the small peptides of this invention are easily modified in composition and conformation to improve further the specific activity of those peptides against FMDV. While the peptides of this invention may be prepared in bacterial hosts employing DNA sequences which code for those peptides, via chemical synthesis, or by some combination of the two, the peptides of this invention that are prepared by chemical synthesis will be more easily purified and advantaged because they are non-biological in origin.

DESCRIPTION OF THE FIGURES

FIGS. 1-2 display the amino acid sequences of the following FMDV subtypes: $O_1K$, $C_1$, $A_5$, $A_{10}$, $A_{12}$, $A_2S$. The sequences of subtypes $O_1K$, $C_1$, $A_5$ and $A_{12}$ are based upon the nucleotide sequences of the gene coding for those proteins. The sequence of subtype $A_2S$ is based on protein sequencing where it appears. Where it appeared appropriate, the sequences of FIGS. 1 and 2 were shifted relative to each other to align them more closely. Such shifts are designated by a dash (- -). The sequences of FIGS. 1 and 2 are numbered so as to include any such shifts. The numbers, therefore, may not be consistent with the actual amino acid sequence numbers for a specific VP1 protein.

DETAILED DESCRIPTION OF THE INVENTION

Referring now to FIGS. 1-2, we have displayed therein the amino acid sequences of protein VP1 of FMDV subtypes $O_1K$, $C_1$, $A_5$, $A_{10}$, $A_{12}$, and $A_2S$. See, e.g., C. Kurz et al., supra (subtype $O_1K$); D. G. Kleid et al., "Cloned Viral Protein Vaccine For Foot-And-Mouth Disease: Response In Cattle And Swine", 214 *Science* 1125-29 (1981) (subtype $A_{12}$); Beck et al., *EMBO Journal* (in press) (subtypes $A_5$ and $C_1$); Boothroyd et al., *Gene*, 17, pp. 153-161 (1982) (subtype $A_{10}$); Strohmaier et al., private communication ($A_2S$).

From a comparison of the amino acid sequences of these FMDV subtypes, we have observed that there is a significant degree of sequence variation in particular well-defined regions of the FMDV polypeptide. This area extends from about amino acid 130 to amino acid 181. We have also determined that each VP1 polypeptide of FMDV subtypes $O_1K$, $C_1$ and $A_5$ is neutralized only by antisera raised against that specific polypeptide. It is not neutralized by antisera raised against either of the other specific polypeptides. Accordingly, we have postulated that the regions of maximum amino acid sequence variation between the FMDV subtypes are the portions of the known polypeptides that carry the specific FMDV antigenic determinants, e.g., from about amino acid 130 to 181 and more preferably from about amino acid 133 to 160 (FIGS. 1 and 2). We also analyzed those regions by conventional α-helix, β-sheet, and reverse turns conformational predictions [e.g., G. E. Schulz and R. H. Schirmer, *Principals Of Protein Structure* 118-120 (1979) and references cited therein].

On the basis of our sequence analysis and conformational predictions, we prepared various peptides corresponding to those areas of maximum amino acid sequence divergence and predicted conformation most likely to be suitable for an antigenic determinant.

We also prepared one peptide outside of the areas of maximum divergence that was near to the COOH terminus of VP1 from subtype $O_1K$, because that area had previously been said to contain the antigenic determinants [Strohmaier et al., supra]. We then tested the peptides for their ability to raise antibodies against VP1 and demonstrated that the peptides of this invention display the antigenicity and specificity of FMDV viral antigens. They are also useful in compositions and in methods for protecting susceptible animals for some time against FMD viral infections.

It should be understood that although the peptides of this invention may be characterized in substantial part by a portion of the region of maximum sequence divergence, other structural and conformational alignment may be necessary for the peptides to display the biological activity and specificity of FMD viral antigens. For example, the peptide must not be too short so as to be unable to attain a conformation necessary for such activity. Therefore, the actual determination of an appropriate peptide, as defined by this invention, requires the simple assays described herein. These assays, in view of the teachings herein, may be performed by those of skill in the art without departing from the scope of this invention.

The particular peptides of this invention are therefore defined as peptides, a substantial part of which comprises a sequence of amino acids selected from the region of maximum sequence divergence between proteins VP1 of the various FMDV subtypes and which are characterized in that antisera raised in rabbits against about 0.2 mg of the peptide (after appropriate coupling) binds to VP1 of the FMDV subtype from which said sequence of amino acids originates at a dilution of at least about 1:100, and more preferably at least about 1:10000, and which antisera is neutralizing to FMDV of that subtype in a baby mouse assay at a dilution of about 1/10 that of the dilution at which it binds to said VP1.

It is, of course, to be understood that while FIGS. 1-2 depict only FMDV subtypes $O_1K$, $C_1$, $A_5$, $A_{10}$, $A_{12}$ and $A_2S$, identical analyses may be employed to identify the location of the antigenic determinant of other FMDV subtypes. It is also to be understood that the peptides of this invention are not limited only to those regions of maximum amino acid sequence divergence between the subtypes of FMDV. Instead, the peptides of this invention may extend outside of that specific region or may include wholly unrelated amino acid sequences or chemical couplings so long as a substantial part of those peptides include sequences from that particular region and those peptides satisfy the other defined requirements of the peptides of this invention.

The specific selection of the particular peptide within the above definition of the peptides of this invention is not critical. Such a selection may be done by taking a number of peptides and testing those peptides as described in this invention for their immunological and biological activity against FMDV.

The peptides or groups of peptides of this invention may then be prepared by conventional synthesis using any of the known peptide synthetic methods including synthesis on a solid support. The peptides of this invention may also be prepared in appropriate hosts transformed with DNA sequences that code for the desired peptide. A combination of such methods may also, of course, be employed. In a preferred embodiment of this invention, chemical synthesis alone is employed. Using that method, the peptides of this invention are additionally advantaged for use in the compositions and methods of this invention because they are easily purified and are not biological in origin. In a more preferred embodiment of this invention, the DNA sequences coding for several of the peptides of this invention are linked together and those sequences are used to transform appropriate hosts to enable the expression of the desired peptides.

The peptides of this invention are useful in compositions and methods for protecting animals against FMDV for at least some period of time. The peptides may be employed in these compositions and methods either alone or together with other peptides of the class defined in this invention in a manner consistent with the conventional utilization of antigens in animal vaccines and methods of treatment. While the compositions and methods of this invention may be characterized by one or more peptides from one FMDV subtype, the most preferred compositions and methods of this invention are characterized by peptides from several FMDV subtypes and serotypes. In this preferred embodiment, the compositions and methods are multivalent.

Although the peptides of this invention may be employed alone in the compositions and methods described herein, they are preferably coupled to one or more carrier proteins before use. Among the carrier proteins usefully employed in this invention are bovine serum albumin (BSA), thyroglobulin (Thyr) and keyhole limpet hemocyanin (KLH). The peptides of this invention are coupled to the carrier protein in various conventional ways. For example, glutaraldehyde [M. Reichlin, "Use Of Glutaraldehyde As A Coupling Agent For Proteins And Peptides", 70 *Methods In Enzymology* 159–165 (1980)], N-ethyl-N'-(3-dimethylaminopropyl)-carbodiimide [T. L. Goodfriend et al., "Antibodies To Bradykinin and Angiotensin: A Use Of Carbodiimides In Immunology", 144 Science 1344–46 (1964)] and a mixture of N-ethyl-N'-(3-dimethylaminopropyl)-carbodiimide and the succinylated carrier protein [M. H. Klapper et al., "Acylation With Dicarboxylic Acid Anhydrides", 25 *Methods Of Enzymology* 531–36 (1972); Goodfriend et al., supra] may be employed. In addition, the peptides of this invention may be polymerized with a conventional polymerization agent, e.g. toluene diisocyanate, before use. E.g., F. Wold, "Bifunctional Reagents", 25 *Methods Of Enzymology* 623–651 (1972).

After preparing the peptide and coupling it to the carrier protein, if desired, the antigen is employed in the methods and compositions of this invention in a conventional manner. For example, the peptide or coupled peptide is usually mixed with one or a combination of well-recognized adjuvants and additives, preferably by first dissolving the peptide, for example, in PBS with 0.1% SDS. In another embodiment of this invention, the peptides may be linked to hydrophobic groups to build the adjuvant into the composition. Of course, it should be understood that the other well-known methods of preparing a composition for treating animals may be employed using the antigenic peptides of this invention.

The above-prepared composition is then employed in a conventional manner to treat animals susceptible to FMDV infections. Such methods of treatment and their dosage levels and requirements are well-recognized in the art and may be chosen by those of skill in the art from available methods and techniques.

In order that the invention herein described may be more fully understood, the following examples are set forth. It should be understood that these examples are for illustrative purposes only and should not be construed as limiting this invention in any way to the specific embodiments recited therein.

EXAMPLE I

Peptides Corresponding to Amino Acid Sequences in Polypeptide VP1 of FMDV Strain $O_1K$

A. Selection Of The Peptides Of This Invention

As described above, we analyzed the amino acid sequences depicted in FIGS. 1-2 and selected the region from amino acid 130 to 181 of VP1 of FMDV subtype $O_1K$ as the region of maximum divergence among the subtypes. Therefore, in accordance with this invention, we determined that this region of the polypeptide carried the FMDV antigen determinants. We then analyzed this region using α-helix, β-sheet and reverse turns conformational predictions [Schultz and Shirmer, supra].

As a result of our analyses, we selected five peptides for synthesis:

| | |
|---|---|
| Peptide FA (AA206-214 of VP1) | Ile—Val—Ala—Pro—Val—Lys—Gln—Thr—Leu |
| Peptide FB (AA152-159 of VP1) | Ala—Gln—Lys—Val—Ala—Arg—Thr—Leu |
| Peptide FC (AA144-151 of VP1) | Leu—Arg—Gly—Asp—Leu—Gln—Val—Leu |
| Peptide FD (AA144-159 of VP1) | Leu—Arg—Gly—Asp—Leu—Gln—Val—Leu—Ala—Gln—Lys—Val—Ala—Arg—Thr—Leu |
| Peptide FE (AA167-181 of VP1) | Ala—Ile—Lys—Ala—Thr—Arg—Val—Thr—Glu—Leu—Leu—Tyr—Arg—Leu—Lys |

We synthesized these peptides via the solution method (BACHEM). In our synthesis, we found it more convenient to synthesize hexadecapeptide FD by combining octapeptides FB and FC, rather than to synthesize peptide FD directly. We also prepared four other peptides from VP1 of FMDV strain $O_1K$:

| | |
|---|---|
| Peptide 1 | AA 141-161 |
| Peptide 2 | AA 135-161 |
| Peptide 3 | AA 134-159 |
| Peptide 4 | AA 140-159 |

We confirmed the structures and purity of our peptides by conventional structural analysis.

Of the five peptides FA through FE, four of them, peptides FB, FC, FD and FE are within the region of maximum sequence divergence, e.g., amino acids 130–181 (FIGS. 1 and 2). *One of the peptides (peptide FA) is outside of that region but it is within an area previously reported to carry the FMDV antigen determinants [Strohmaier et al., supra]. All of peptides 1 through 4 are within the area of maximum sequence divergence.

*Peptide FE contains one amino acid different than the corresponding amino acid of VP1, subtype $O_1K$. In peptide FE, amino acid 180 is leucine, while in VP1 it is methionine (FIGS. 1 and 2). We do not believe that this exchange is critical.

B. Immunological Activity of the Peptides of this Invention

1. Coupling of Peptides to Carrier Proteins

We coupled the above-described proteins to the carrier proteins BSA, Thyr, KLH or their succinylated counterparts by various known methods using glutaraldehyde (Glu) or N-ethyl-N'-(3-dimethylaminopropyl)-carbodiimide (CDI). We coupled the peptide and carrier protein in several ways.

(a) With Glu

We dissolved 2 mg of peptide in 10 μl H₂O and added 15 mg of carrier protein in 2 ml sodium phosphate buffer (0.1M, pH=7.0). We then added 1 ml of a water solution of Glu (21 mM) dropwise over 1 h at room temperature. We allowed the mixture to stand overnight and then dialyzed it against PBS.

(b) With CDI

In the case of a non-succinylated carrier protein, we dissolved 2 mg of peptide in 10 μl H₂O and 15 mg of carrier protein in 1 ml of sodium phosphate buffer (0.1M, pH=6.0). We then added a solution of 120 mg CDI in 150 μl H₂O dropwise over 1 h at room temperature. After shaking for 1 h at room temperature, we allowed the reaction mixture to stand overnight and dialyzed it against PBS.

In the case of a succinylated carrier protein, we first prepared a solution of 20 mg of carrier protein in 200 μl H₂O and added 100 mg succinic anhydride a little at a time while maintaining the pH of the reaction mixture between about 7.0 and 7.2 with NaOH. The addition took about 1 h. We then lyophilized the mixture and used 1.5 mg of it as above for CDI coupling to the peptide.

2. Polymerization of Peptides with Toluenediisocyanate

We polymerized the above-described peptides with toluenediisocyanate (TDI) using conventional methods.

3. Inoculation of Test Animals a. Rabbits

We dissolved the free peptide or modified peptide antigens in PBS with 0.1% SDS and mixed the resulting solutions with complete Freund adjuvant at a 1:1 ratio. We employed doses of 400 μg peptide and 1 mg carrier protein or 1 mg free peptide in a total volume of 1.0 ml for subcutaneous injection into rabbits. Four weeks later (day 28), we took blood samples from the rabbits and assayed the sera using the various assays described below. The results of the assays are displayed in Tables I, II and IV.

After taking the above-described blood samples, we repeated the injection (the adjuvant for this booster was incomplete Freund adjuvant) and ten days later (day 38) again took blood samples from the rabbits and assayed the sera as before. The results are displayed in Tables I, II and IV. Finally, for rabbits 6, 17, 21, 24 and 26, after taking the last described blood samples, we repeated the injection (the adjuvant for this booster was incomplete Freund adjuvant) and ten days later (day 48) again took blood samples from the rabbits and assayed the sera as before. The results are displayed in Table V.

b. Cattle

We again dissolved the free peptide or modified peptide antigens in PBS with 0.1% SDS and mixed the resulting solutions with incomplete Freund adjuvant at a 1:1 ratio. We employed doses of 1.2 mg peptide and 3 mg carrier protein in a total volume of 3 ml for injection intramuscularly into cattle. Seven weeks later, we took blood samples from the cattle and assayed the sera using the Elisa assay. The results of the assays are displayed in Table III.

After taking the above-described blood samples, we repeated the injection and fourteen days later again took a blood sample and assayed the sera. The results of the assays are displayed in Table III.

c. Assays i. Elisa

Microtiter plates (Nunc) were coated with peptide (5 μg/well) or authentic VP1 (0.25 μg/well) or FMD virus (0.05 μg/well) and incubated overnight at room temperature. After washing the wells two times with PBS, we saturated the wells with 1% BSA in PBS (30 min at 37° C.) and we added 50 $\mu$l sera to the wells (dilutions 1:10 up to 1:1000). After incubation for two hours at 37° C., we washed the wells five times with PBS/Triton X100 and we incubated the wells for an additional two hours with peroxidase-labelled goat-anti-rabbit IgG at a ratio of 1:500 in 1% BSA/PBS. After repeated washings with PBS/Triton X100, we added to each well 50 $\mu$l of a solution of 0.4% o-phenylenediamine and 0.012% $H_2O_2$ in 0.1M phosphate-citrate-buffer. After 30 min, we stopped the enzyme reactions and determined the assay titer with a Titertek Multiscan photometer at 492 nm.

We therefore determined by the above-described assay if antisera raised by a peptide in an animal binds to the peptide and to authentic VP1. In addition, by using dilutions of the sera, we obtain an indication of the level of the antisera.

ii. Baby mice assay

The baby mice assay is a conventional assay. E.g., H. H. Skinner, 1 *Proc. 15th Int. Det. Congr.* Part 1, 195 (1952). In this assay, the antisera raised in rabbits as before was mixed at various dilutions with FMDV of the appropriate subtype and the mixture was incubated. Baby mice are then injected with the antisera-virus mixture. Since FMDV infection kills baby mice, if active virus is present in the injected mixture (e.g., the virus has not been neutralized by the antisera raised by the peptides of this invention), the mice will die. Accordingly, the assay is a measure of the virus-neutralizing activity of the antisera produced by the peptides of this invention. The results of the baby mice assays are shown in Tables IV and V.

TABLE I

| Rabbit No. | Peptide | Carrier | Method for Coupling | Assay after 1st booster peptides | Assay after 1st booster VP1 | Assay after 2nd booster peptides | Assay after 2nd booster VP1 |
|---|---|---|---|---|---|---|---|
| 4 | FA/FB/FC | BSA | Glu | 1:100 | 1:20 | >1:100 | 1:40 |
| 5 | FA/FB/FC | Thyr | Glu | 1:100 | 1:20 | >1:100 | 1:40 |
| 6 | FA/FB/FC | KLH | Glu | 1:100 | 1:30 | >1:100 | 1:50 |
| 7 | FA/FB/FC | succ. BSA | CDI | <1:10 | <1:10 | 1:20 | <1:10 |
| 8 | FA/FB/FC | succ. Thyr | CDI | <1:10 | <1:10 | <1:10 | <1:10 |
| 9 | FA/FB/FC | succ. KLH | CDI | <1:10 | 1:20 | <1:10 | 1:50 |
| 10 | FA/FB/FC | BSA | CDI | 1:10 | 1:100 | 1:80 | 1:400 |
| 11 | FA/FB/FC | Thyr | CDI | 1:100 | 1:50 | >1:100 | 1:200 |

TABLE I-continued

| Rabbit No. | Peptide | Carrier | Method for Coupling | Assay after 1st booster peptides | VP1 | after 2nd booster peptides | VP1 |
|---|---|---|---|---|---|---|---|
| 12 | FA/FB/FC | KLH | CDI | 1:10 | 1:50 | 1:10 | >1:100 |

TABLE II

| Rabbit No. | Peptide FA | Carrier | Method for Coupling | Assay after 1st booster peptides | VP1 | after 2nd booster peptides | VP1 |
|---|---|---|---|---|---|---|---|
| 13 | FE | — | — | <1:10 | <1:10 | 1:10 | 1:10 |
| 14 | FD | — | * | <1:10 | <1:10 | <1:10 | <1:10 |
| 15 | FE | — | * | 1:100 | <1:10 | >1:100 | <1:10 |
| 16 | FD/FE | Thyr | Glu | >1:100 | 1:20 | >1:100 | 1:100 |
| 17 | FD/FE | KLH | Glu | >1:1000 | >1:1000 | >1:1000 | >1:10$^4$** |
| 18 | FD/FE | succ. Thyr | CDI | 1:100 | 1:10 | >1:100 | 1:10 |
| 19 | FD/FE | succ. KLH | CDI | 1:50 | <1:10 | 1:100 | <1:10 |
| 20 | FD/FE | Thyr | CDI | 1:50 | <1:10 | 1:100 | <1:10 |
| 21 | FD/FE | KLH | CDI | 1:100 | >1:10$^3$ | >1:100 | >1:10$^4$** |
| 22 | FD | — | — | 1:40 | <1:10 | 1:100 | <1:10 |
| 23 | FD | Thyr | Glu | >1:100 | >1:100 | — | — |
| 24 | FD | KLH | Glu | >1:100 | >1:100 | — | — |
| 25 | FE | Thyr | Glu | >1:100 | >1:100 | — | — |
| 26 | FE | KLH | Glu | >1:100 | >1:10 | — | — |

*peptide polymer with TDI
**When assayed against VP1 from either FMDV subtype A$_5$ or C$_1$, the result was <1:10. To determine the relative contributions of antisera raised against individual peptides FD and FE, we separated the antisera by affinity chromatography and reassayed the two antisera:

| Antisera | Peptide | VP1 |
|---|---|---|
| Antisera to FD | >>1:1000 | >1:100 |
| Antisera to FE | >1:1000 | <1:50 |

TABLE III

| Cattle No. | Peptide FD | Carrier | Method for Coupling | Assay after 1st booster peptides | VP1 | after 2nd booster peptides | VP1 |
|---|---|---|---|---|---|---|---|
| 1 | FD/FE | Thyr, succ. Thyr | Glu/CDI | <1:10 | 1:10 | 1:10 | 1:10 |
| 2 | FD/FE | KLH, succ. KLH | Glu/CDI | <1:10 | <1:100 | 1:10 | 1:200 |
| 3 | FD/FE | KLH, succ. KLH | Glu/CDI | <1:10 | >1:10 | <1:100 | 1:50 |

TABLE IV

| rabbit no. | first injection | baby mice assay LD$_{50}$ second injection | third injection |
|---|---|---|---|
| 11 | — | — | <1:4 |
| 12 | — | — | <1:4 |
| 17 | 1:32 | 1:256 | 1:1782 |
| 21 | 1:28 | 1:124 | 1:1024 |
| 23 | — | 1:8 | — |
| 24 | — | 1:14 | — |

TABLE V

| Rabbit No. | Peptide | Carrier | Method for Coupling | 10 days After Third Injection ELISA Assay VP1 | Baby Mice Assay SNT |
|---|---|---|---|---|---|
| 6 | FA/FB/FC | KLH | Glu | 1:50 | <1:2 |
| 17* | FD/FE | KLH | Glu | 1:25000 | >1:4000** |
| 21* | FD/FE | KLH | CDI | >1:15000 | >1:4000** |
| 24* | FD | KLH | Glu | 1:2000 | >1:3000** |
| 26*** | FE | KLH | Glu | 1:10 | <1:2 |

*Immune to FMDV upon challenge.
**When assayed against subtype A$_5$ the result was <1:4 and when assayed against subtype C$_1$ the result was 1:100.
***Showed virus multiplication upon challenge. Not immune.

d. Results of Assays

The Elisa assays demonstrated that peptides FA, FB and FC in combination raised antibodies to VP1 at a very low level. Moreover, these antisera are substantially non-neutralizing in the baby mouse assay. In addition, the assays demonstrate that peptide FE also raises antibodies to VP1 at a very low level.

Peptide FA is, of course, outside of the region selected by us on the basis of maximum sequence divergence (supra). Peptides FB, FC and FE are within those regions of maximum sequence divergence. The lack of antigenic activity of these peptides is, therefore, likely due to their inability to attain a correct conformation. Of course, it should be understood that if peptides FB, FC or FE were modified to lengthen or shorten them or to provide other means for them to attain the correct conformation, they may fall within the peptide definition of this invention. This possibility is supported by the high antigenic and neutralizing activity of peptide FD which is a combination of peptides FB and FC.

The Elisa assays also demonstrated that peptide FD after coupling, alone or with peptide FE, is highly antigenic in character. E.g., rabbits 23, 24, 17 and 21. Moreover, the baby mouse assays demonstrate that the antisera raised by FD peptide alone or a combination of peptides FD and FE are able to neutralize FMDV. Positive results were also observed with peptides 1 through 4.

The assays demonstrated as well that the antisera raised by the peptides of this invention are specific.

They do not bind to VP1 of the FMDV subtype $A_5$ and bind at about a 1% level to VP1 of FMDV subtype $C_1$.

EXAMPLE II

Peptides Corresponding to Amino Acid Sequences in Polypeptide VP1 of FMDV Strain $C_1$ Using the procedure described in Example 1, we also prepared and assayed peptides from the regions of VP1 of FMDV Subtype $C_1$, similar to those we employed from VP1 of FMDV subtype $O_1K$. These peptides displayed the antigenicity of FMDV antigens in much the same way that our $O_1K$ peptides did, except that the levels of neutralizing antibodies raised by the $C_1$ peptides were lower.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which have been presented hereinbefore by way of example.

We claim:

1. A peptide displaying the antigenicity of a FMD viral antigen selected from the group of peptides consisting of: Leu—Arg—Gly—Asp—Leu—Gln—Val—Leu—Ala—Gln—Lys—Val—Ala—Arg—Thr—Leu, Val—Pro—Asn—Leu—Arg—Gly—Asp—Leu—Gln—Val—Leu—Ala—Gln—Lys—Val—Ala—Arg—Thr—Leu—Pro—Thr, Arg—Tyr—Asn—Arg—Asn—Ala—Val—Pro—Asn—Leu—Arg—Gly—Asp—Leu—Gln—Val—Leu—Ala—Gln—Lys—Val—Ala—Arg—Thr—Leu—Pro—Thr, Cys—Arg—Tyr—Asn—Arg—Asn—Ala—Val—Pro—Asn—Leu—Arg—Gly—Asp—Leu—Gln—Val—Leu—Ala—Gln—Lys—Val—Ala—Arg—Thr—Leu, and Arg—Val—Pro—Asn—Leu—Arg—Gly—Asp—Leu—Gln—Val—Leu—Ala—Gln—Lys—Val—Ala—Arg—Thr—Leu.

* * * * *